(12) United States Patent
Fujisato et al.

(10) Patent No.: US 8,323,881 B2
(45) Date of Patent: Dec. 4, 2012

(54) METHOD OF CELL INJECTION INTO BIOTISSUE AND APPARATUS THEREFOR

(75) Inventors: Toshiya Fujisato, Suita (JP); Akio Kishida, Suita (JP); Soichiro Kitamura, Suita (JP)

(73) Assignees: Japan as represented by President of National Cardiovascular Center, Suita-shi (JP); Nipro Corporation, Osaka-shi (JP)

( * ) Notice: Subject to any disclaimer, the term of this patent is extended or adjusted under 35 U.S.C. 154(b) by 1686 days.

(21) Appl. No.: 10/562,833

(22) PCT Filed: Jul. 2, 2004

(86) PCT No.: PCT/JP2004/009436
§ 371 (c)(1),
(2), (4) Date: Sep. 6, 2006

(87) PCT Pub. No.: WO2005/002651
PCT Pub. Date: Jan. 13, 2005

(65) Prior Publication Data
US 2009/0155760 A1    Jun. 18, 2009

(30) Foreign Application Priority Data
Jul. 4, 2003    (JP) .................................. 2003-191778

(51) Int. Cl.
A01N 1/00    (2006.01)
C12M 1/00    (2006.01)
C12M 3/00    (2006.01)
C12M 1/36    (2006.01)
C12M 1/38    (2006.01)

(52) U.S. Cl. .................... 435/1.1; 435/284.1; 435/285.2; 435/286.2

(58) Field of Classification Search .................... None
See application file for complete search history.

(56) References Cited

U.S. PATENT DOCUMENTS
2001/0049532 A1 *  12/2001  Saishin et al. ................ 606/107

FOREIGN PATENT DOCUMENTS
| JP | 8-322568 A | | 12/1996 |
| JP | 8 322568 A | * | 12/1996 |
| JP | 2001-46500 A | | 2/2001 |
| JP | 200146500 A | * | 2/2001 |
| JP | 2001-252300 A | | 9/2001 |

* cited by examiner

Primary Examiner — Chris R Tate
Assistant Examiner — Russell Fiebig
(74) Attorney, Agent, or Firm — Millen, White, Zelano, Branigan, P.C.

(57) ABSTRACT

A method of injecting cells into a biological tissue comprising thrusting injection needle (200) under microvibration into tissue (5) secured by suction to tissue suction means (210) and effecting injection of a cell suspension into the tissue through the needle. There is also provided an apparatus for cell injection into the biological tissue.

5 Claims, 2 Drawing Sheets

METHOD OF CELL INJECTION INTO BIOTISSUE AND APPARATUS THEREFOR

FILED OF THE INVENTION

This invention is in the field of regenerative medical technology in which the function of a particular organ or tissue of a patient is normalized by transplantation when the function is lost or otherwise in disorder. More particularly it relates to a method and system for injecting cells into biological tissues to be transplanted.

BACKGROUND ART

For regenerative treatments, native tissue segments of human or mammalian origin have been used clinically as such or after decellularizing or treating with cell-fixing agents such as glutraldehyde. It is advantageous in the regerative treatment to use a regeneratable hybrid tissue prepared by injecting autologous cells of the recipient into the tissue and allowing the cells to grow therein. This method may not only avoid recipient's immune response to the transplanted tissue but also promote autogenesis of the transplanted tissue.

In the preparation of the regeneratable hybrid tissues, a cell suspension is injected manually using a syringe. However, many transplatable tissues have elastically deformable surfaces and, therefore, it is not easy even for skilled operators to pierce the tissue with a syringe needle accurately and precisely in position.

A method and device adapted for injecting medical solutions and other liquid into such elastically deformable tissues is disclosed in JP-A-03322568 and JP-A-200146500. The method and device injects a liquid while vibrating the needle ultrasonically.

In the preparation of the regeneratable hybrid tissues, it is imperative to inject a cell suspension into the tissue in a volume in the order of microliters at many target positions space apart a distance in the order of micrometers with a distribution density which may often reach up to several thousands per square centimeter. It will be impossible in practice to prepare such a regeneratable hybrid tissue with the known method and device by simply vibrating the needle.

There is another problem associated with the known method and device. Regeneratable hybrid tissues are often prepared from pulsating mammalian heart walls or relatively thin blood vessel walls. Since these tissues may move back and forth in the direction perpendicular to the general plane of the tissue, it is difficult to locate the vibrating needle tip at a desired depth and the needle tip may often penetrate through the tissue thoroughly by the vibration.

DISCLOSURE OF THE INVENTION

In order to eliminate or ameliorate the above and other problems, the method and system of the present invention is characterized by holding at least a portion of elastically deformable tissue surface by suction with tissue suction means, piercing the tissue with a microvibrating needle, and injecting a cell suspension through the needle at a desired position within the tissue.

In order to inject the cell suspension in a metered volume, the method and system of the present invention utilizes means for precisely metering the cell suspension in combination with the microvibrating needle.

In order to inject the cell suspension into a desired position within the tissue precisely and automatically, the method and system of the present invention utilizes means for automatically positioning the needle tip at a particular point in the three dimensional coordinates Using the method and system of the present invention, (1) it is possible to inject cell directly into a site of recipient that needs thereof during a surgical operation, (2) it is possible to treat either allogenic soft tissues from brain death or organ death donors or xenogenic soft tissues of porcine or bovine origin, and (3) it is possible to inject cells into artificial or synthetic tissues as well.

DESCRIPTION OF PREFERRED EMBODIMENTS

Figure 1:
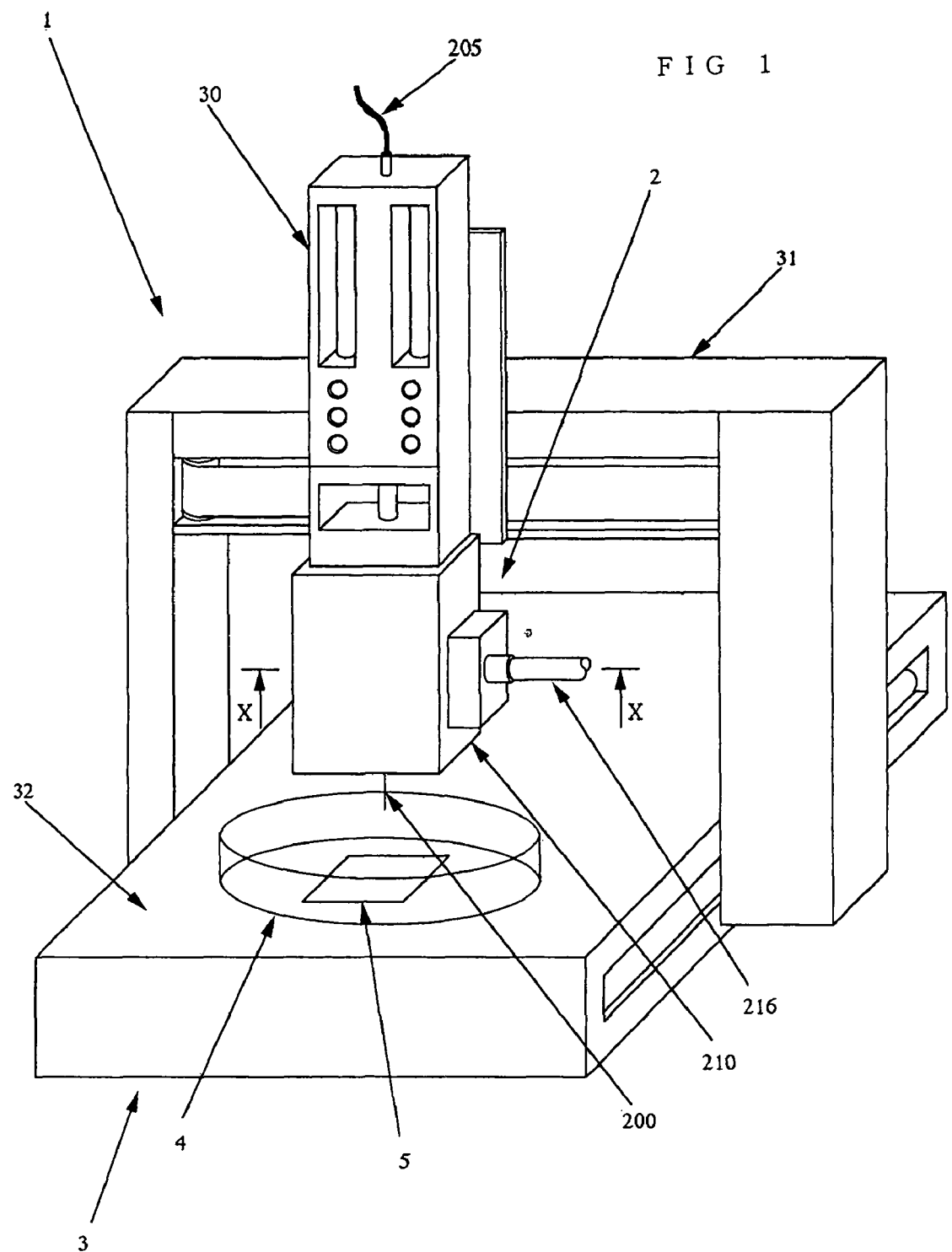
FIG. 1 is a perspective view of the entire system for automatic injection according to the present invention.

Now a preferred embodiment will be described by making reference to the accompanying drawings. FIG. 1 shows the entire system 1 for automatic injection of cells according to the present invention. The system 1 comprises an injection device 2 provided with a microbivrating needle 200. The system 1 also comprises a device 3 for precisely positioning the injection device 2 in three-dimensional directions.

The microvibrating injection device 2 comprises, as described below in detail, a vibrating needle 200 provided with a microvibrator 202 and a suction housing 210 for holding tissue segment 5 by suctioning the tissue surface in place for piercing the tissue with the needle 200 centrally and slidably extending through the suction housing 210.

The three-dimensional positioning device 3 is configured to displace the injection device 2 mounted thereon horizontally in a plane at a particular point in both X and Y coordinate directions accurately. The device 3 also move the injection device 2 vertically so that the needle 200 can pierce the tissue in a predetermined depth precisely. Such positioning devices are well known in the art and commercially available.

The positioning device 3 shown in FIG. 1 comprises a frame member 31 on which a position controller 30 for positioning the injection device 2 in the Z coordinate direction is movably mounted. The positioning device 3 also comprises a bed 32 for mounting a tissue container 4 containing a tissue segment 5. The frame member 31 comprises a pair of legs and a cross-bar secured between legs as shown. The controller 30 is slidable on the cross-bar in the X coordinate direction horizontally and moves the injection device 2 in the Z coordinate direction vertically The frame member 31 carrying the controller 30 is movable along the side edges of the bed 32 in the Y coordinate direction.

Now, the method of injecting cells into a tissue segment 5 will be described by making reference to the drawings.

The tissue segment 5 is placed in the container 4 while keeping wet or intact state. Then the container 4 is secured on the fixing bed 3 using a fixture (not shown). The positioning device 3 includes self-contained control means (not shown) for controlling the movement of both of the frame member 31 and the position controller 30 in the X, Y and Z coordinate directions. The data concerning desired positions and depth of the tissue to be pierced may be inputed in the control means.

Specifically, the vibrating needle 200 is located just above the tissue segment 5 by manually moving the frame member 31 and the injection device 2 horizontally and data concerning the position in X and Y directions at this moment are inputed in the control means as the reference position. Then the injection device 2 is gradually lowered manually until the needle 200 just contact with the surface of the tissue segment 5. The height of needle 200 at this moment is also inputed in the control means as the reference position in the Z direction.

Then the suction housing 211 (see, FIG. 2) is lowered to contact with the tissue 5 with the needle 200 being retracted to a position flush with or slightly above the bottom surface of the housing. The interior of the housing 211 is kept under negative pressure before lowering to hold the tissue 5 against the bottom of the suction housing 211 by suction force.

The vibrating needle 200 is movable in vertical direction independently from the suction housing 210. The control means determines a distance in which the needle tip extends beyond the bottom of the suction chamber. This distance corresponds to the depth that the needle tip penetrate into the tissue. When the needle tip extends 1 mm, for instance, beyond the bottom of suction housing, then the needle tip penetrates into the tissue to a depth of 1 mm.

It is important at this moment that the tissue segment 5 is securely held on the bottom surface 212 by a suction force exerted through a plurality of holes 213 and that the needle tip penetrates the tissue while vibrating. This enables the position of upper surface of the tissue 5 which is flush with the bottom surface of suction housing 210 to be detected and also enables the penetration depth of the needle into the tissue to be accurately and precisely determined. Suctioning the tissue against the bottom surface 210 of suction housing assists to hold the tissue under-tension and, therefore, the needle can penetrate into otherwise deformable tissue segment to a desired depth accurately and precisely.

The injection needle is in fluid communication with means for precisely metering a cell suspension (not shown) and injects the metered volume of the cell suspension. Thereafter the needle is retracted to the original position and the negative pressure within the suction chamber 211 is released to detach the tissue 5 from the suction housing 210. Then the injection device 2 is elevated away from the tissue. The three dimensional positioning device 3 and its control means repeat the above procedure as desired at various positions of the tissue 5 according a program for scanning over the tissue and these positions in the X and Y coordinates are determined relative to the reference position originally inputed in the control means.

Figure 2:
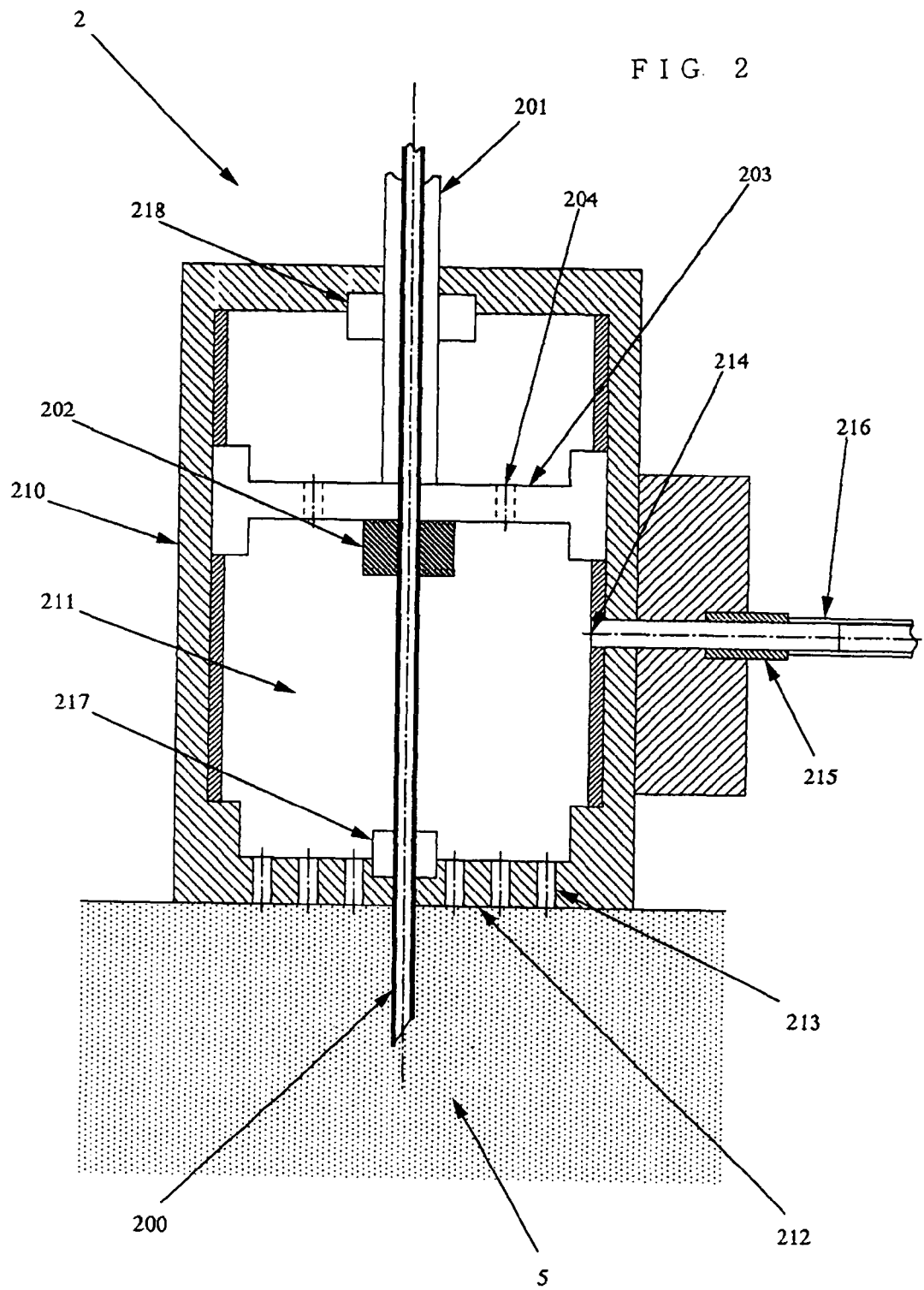
FIG. 2 is a cross-sectional view of the system taken along the line X-X of FIG. 1.

Turning to FIG. 2, the suction housing 210 is shown in cross-section taken along line X-X of FIG. 1. The injection device 2 comprises an injection needle provided with a vibrator 202 and a suction housing 210 enclosing the needle for holding the tissue segment 5. The needle 200 is secured through a flange or piston 203 that allows the needle to slide in the housing 210 vertically independently from the housing. Specifically the housing 210 is directly carried by the positioning device 30 that controls the position of the housing 2 in Z coordinate direction while the needle 200 is friction fitted in the mating bore of the needle guide rod 201 which, in turn, is coupled to the means for elevating and descending the guide rod 201 (not shown) contained in the positioning device 30. The needle 200 is connected in fluid communication with the means for precisely metering the cell suspension (not shown).

The metering means may be of conventional type and is commercially available. The metering means may be disposed internally or externally of the injection device. In the embodiment shown in FIG. 1, the metering means is connected externally to the injection device 2 via flexible tubing 205. The external connection of the metering means simplifies the construction of the injection device and facilitates the maintenance or operation of both of the injection device and the metering means, particularly when filling and refilling the metering means with fresh cell suspension. This arrangement not only contributes to the reliability of the entire system and also eliminates need for those accessories which are otherwise susceptible to failure or malfunction.

The suction housing 210 defines the suction chamber 211 therein and an opening 214 communicating with an external pressure source (not shown) to create negative or positive pressure within the suction chamber 211. The pressure source may be a pump or a pair of negative and positive tanks. In the embodiment shown in FIG. 2, the pressure source is connected to the opening 214 in fluid communication via a plug 215 and a tubing or hose 216 to create negative pressure and positive pressure or the atmospheric pressure within the suction chamber 211 alternately for attracting and detaching the tissue segment to and from the suction housing 210.

The suction housing 210 defines a plurality of throughholes 213 in the bottom wall for applying negative or positive pressure to the tissue segment 5. The outer face of the bottom wall is flat in the X and Y coordinate directions to attract the tissue outer surface in alignment with the bottom face 212 of the suction housing 210.

The top and bottom walls of the suction housing 210 are provided with sliding sleeve rings 217 and 218, respectively to maintain the chamber 211 air tight. The needle 200 is slidably received in the bottom sleeve ring 217 while maintaining air tight contact between them. Similarly, the top sleeve ring 218 slidably receive the needle guide rod 201 while maintaining air tight contact between them.

As described above, the needle 200 is secured to the flange or piston 203 that reciprocates vertically in the suction chamber 211. The reciprocating flange 202 is connected, in turn, to the needle guide rod 201 carrying the needle 200. Thus the needle and guide rod assembly may be elevated and descended within the suction chamber 211 by its own drive means self-contained in the positioning device 30 independently from the movement of the suction housing 210. However, how long the needle tip should be extended or retracted is determined based on the bottom surface 212 of the housing 210. Preferably, the flange or piston 203 has one or more vent holes to equalize the pressure in the suction chamber 211 above and below the flange 203. This facilitates the reciprocation of the flange 203 in the suction chamber.

The needle vibrator 202 is disposed around the needle 200 below the flange 203, preferably adjacent to the flange. Any of known microvibrators may be employed including, mechanical vibrators, electrical oscillators, ultrasonic vibrators and the like.

The invention is not limited to the embodiments specifically shown and described herein. For example, tissue segments could be held in position by using adhesives having no adverse affects to the tissue or magnetically attracting a container for the tissue.

EXAMPLES

Example 1

Using the method and system of the present invention, a cell suspension (105 cell/ml) was automatically and precisely injected into porcine heart muscle at 2,500 locations each spaced apart a distance of 200 μm in the area of 1×1 cm square at a dose of 200 picoliters/location by inserting the injection needle a depth of 2 mm.

Example 2

Using the method and system of the present invention, a cell suspension (105 cells/ml) was automatically and precisely injected into pulsating porcine heart wall at 50 locations arranged in row each spaced apart a distance of 200 μm at a dose of 100 picoliters/location by inserting the injection needle a depth of 5 mm.

The invention claimed is:

1. A system for injecting cells into a biological tissue segment comprising an injection needle in fluid communication with a device for conveying a cell suspension to said needle from the source thereof;

a means for generating microvibration in said needle;

a support member for holding said tissue on a first flat face thereof, said support member being a part of a housing defining a chamber in the interior thereof and defining a plurality of perforations extending through said first flat face, said needle extending centrally through said support member and said chamber;

a means for creating negative and positive pressures within said chamber;

a means for advancing and retracting said needle a predetermined distance across the first flat face of said support member;

a means for infusing a predetermined volume of said cell suspension into said tissue through said needle when the distal end thereof extends said predetermined distance beyond said first flat face;

a means for positioning and repositioning said needle carried on said support member, when the needle is retracted, to a series of points on the tissue according to their X and Y coordinates.

2. The system according to claim 1, wherein said needle and said microvibration means are secured to a piston that reciprocates in said chamber.

3. The system according to claim 1, wherein said means for advancing and retracting said needle are mounted on said housing on the side opposite to said tissue support member and wherein said means for positioning and repositioning the needle displace said housing relative to the X and Y coordinates of the tissue.

4. The system according to claim 1, wherein said means for infusing the cell suspension comprises a fluid metering device connected to the needle in fluid communication externally of said housing.

5. The system according to claim 1, wherein said microvibration means comprises a mechanical vibrator, an electrical oscillator or an ultrasonic vibrator.

* * * * *